United States Patent [19]

Bartholomew

[11] 4,274,406

[45] Jun. 23, 1981

[54] TRACHEOTOMY MASK

[76] Inventor: Victor L. Bartholomew, 40843 Marion, Hemet, Calif. 92343

[21] Appl. No.: 72,128

[22] Filed: Sep. 4, 1979

[51] Int. Cl.³ .......................................... A61M 15/00
[52] U.S. Cl. .......................... 128/206.21; 128/204.25; 128/912
[58] Field of Search ............... 128/206.21, 206.28, 128/207.11, 207.12, 207.14, 207.15, 207.16, 207.17, 912, 205.25, 204.26, 204.25

[56] References Cited

U.S. PATENT DOCUMENTS

| | | | |
|---|---|---|---|
| 3,236,236 | 2/1966 | Hudson | 128/207.17 |
| 3,461,877 | 8/1969 | Morch | 128/207.14 |
| 3,814,103 | 6/1974 | Fettel et al. | 128/207.18 |
| 3,824,999 | 7/1974 | King | 128/207.17 |
| 4,045,058 | 8/1977 | Eross | 128/207.14 X |
| 4,152,017 | 5/1979 | Abramson | 128/207.14 X |

Primary Examiner—Henry J. Recla
Attorney, Agent, or Firm—Seiler & Quirk

[57] ABSTRACT

An oxygen delivery device such as an oxygen mask or tracheotomy mask includes a mask body having an enlarged port, an adapter secured at the port end rotatable 360° therearound, an orifice on the adapter offset relative to the axis of rotation, and a pipe having one end rotatably secured at the orifice and which pipe is along its length.

7 Claims, 6 Drawing Figures

TRACHEOTOMY MASK

BACKGROUND OF THE INVENTION

A popular tracheotomy mask, and one which has gained wide use and recognition in the respiratory therapy field is described and shown in U.S. Pat. No. 3,236,236 (Hudson). Although such a mask is relatively inexpensive, and disposable, intended for single patient use, and is comfortable because of the relatively soft, flexible plastic body which is positioned on the patient's neck, it is somewhat limited in the direction or angle at which an oxygen supply tube can be secured on the device. Specifically, the Hudson mask incorporates a tubing adapter which is rotatable on the mask about a single axis, and a pipe extends at a right angle from the adapter. Connecting the oxygen supply tubing to the right angle pipe is sometimes inconvenient, since the end of the pipe is usually not directed toward the oxygen supply source. A more recent device is disclosed in U.S. Pat. No. 3,824,999 (King) incorporating a spherical tubing adapter which is rotatable between rings in a universal fashion, thereby providing a substantially greater flexibility and convenience in attaching an oxygen supply tubing to the tubing adapter pipe.

The tracheotomy mask of the present invention provides a still further advantage over previous devices. Because of its construction, it allows even greater flexibility than the King mask in providing a two-way rotation, combined with an angled pipe, so that even greater pipe direction selection is possible. In addition, because of its construction, the present device is relatively simple to assemble. These as well as other advantages will be evident from the following detailed description.

SUMMARY OF THE INVENTION

The tracheotomy mask of the present invention incorporates a soft, flexible mask body for being secured against a patient's throat, a fitting member or adapter which is rotatably secured on the body, and a curved or angled pipe which is rotatably secured on the adapter. Both the adapter and pipe rotate about single, but different, axes which form an acute angle with one another. With the pipe being angled, because of the two-way rotation, the pipe end, to which an oxygen supply hose or tube is attached, can be adjusted to any desired direction, thereby making the device extremely convenient to use.

DETAILED DESCRIPTION OF THE INVENTION

Figure 1:
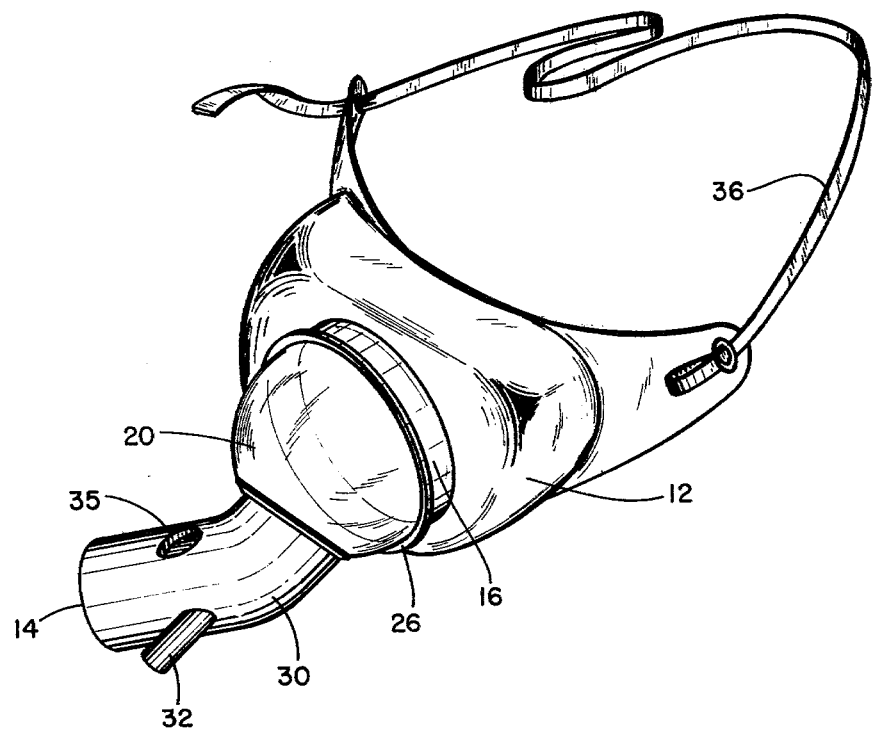
FIG. 1 is a perspective view showing the tracheotomy mask of the invention.
Figure 2:
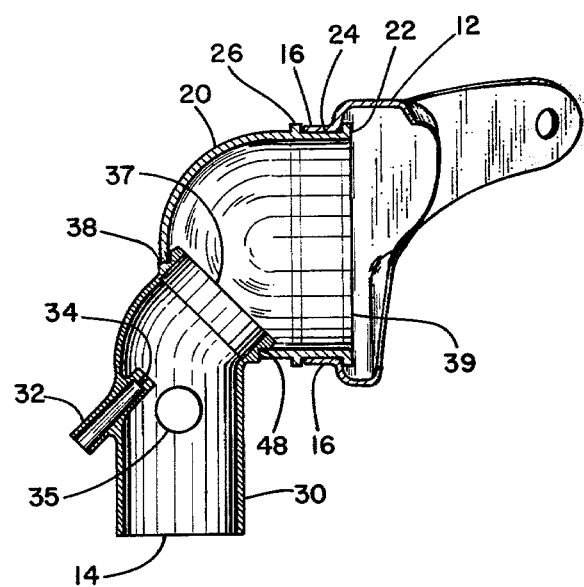
FIG. 2 is a side sectional elevation of the mask.

In FIGS. 1 and 2 the device of the invention is shown in detail comprising a body member 12 to which is attached the fitting member or adapter 20. The body member is preferably of a relatively soft, flexible material such as polyvinyl chloride, having a peripheral edge which can engage a patient's throat to form a gas-tight seal. To the body member is attached a flexible strap 36, which may be elastic, and which can be tightened so that the body member can be secured on the patient's throat. Such a body member is disclosed in the aforesaid Hudson patent, and the description thereof is incorporated herein by reference. However, other suitable tracheotomy body members may also be used, so long as they are adapted to receive the rotatable adapter as will be described hereinafter.

At the forward portion or front of the body member is an enlarged port 39, defined by a guide lip 16, which is an integral part of the body member, and extends forwardly to form an annular ring, and in which the adapter is secured. Thus, the enlarged forward port of the body member is defined by the interior surface of the circular lip 16.

In engaging adapter 20, lip is slightly stretched so as to be received and seated within circular channel 24 lying between guides 22 and 26, in the form of flanges or walls extending outwardly from the adapter and acting as guides for restricting movement of the adapter into or away from body member 12. Thus, the guides allow the adapter to be moved only by rotation about a single axis. The extent that lip 16 projects forwardly from the body member is such that it conveniently fits into the channel 24, which channel then acts as a guide for the lip. Adapter 20 is preferably formed of a rigid plastic, such as rigid polyethylene or PVC, and having a surface characteristic for being readily slidable relative to the flexible plastic of which the body member is composed. Accordingly, although lip 16 will be slightly expanded as it is seated into channel 24, thereby providing a substantially gas-tight seal between the lip and channel surface, adapter 20 is readily rotatable within the lip. This feature can be more readily observed in FIG. 2, with adapter 20 preferably being rotatable about a single axis extending normal to a plane across port 39 defined by lip 16. In other words, as FIG. 2 is viewed, with port 39 lying along a vertical plane, adapter 20 is rotatable about a horizontal axis. Such a rotation of the adapter and its relationship to lip 16 and rotation thereabout is substantially like that described in the aforesaid Hudson patent.

Although the preferred embodiment is so described and shown, other modifications may be used. For example, the adapter may comprise two portions, one which is non-rotatable and secured to the body member, and the other portion being rotatable, again along a single axis, and perpendicular to a plane extending vertically across port 39. However, such an embodiment would require adapter 20 to be constructed of two parts, one rotatable relative to the other, which would be likely more difficult and costly to produce than the preferred embodiment described hereinabove.

Pipe 30 is open at both opposite ends 37 and 14. The pipe is secured at port 38 of the adapter, and rotatable at that port. Observing also FIGS. 5 and 6, pipe 30 is provided with a groove 48 defined between a pair of bosses or rims 44 and 46. With port 38 of adapter 20 being circular, and with groove 48 also being circular, and of just slightly less diameter than the port, the circular port surface rotatably fits in the groove. Moreover, the rims 44 and 46 act as guides for the rotating pipe, as well as preventing other substantial movement of the pipe relative to the adapter, thus securing the fit between the two components. With the adapter 20 being produced of a substantially rigid plastic material, the pipe is preferably made from a somewhat more flexible material, such as polyethylene, which can be deformed under pressure. Thus, the pipe can be snapped into place by being slightly deformed at pipe end 37 so that rim 44 can pass into port 38 of the rigid adapter, and then allowed to expand back to its original position, which will secure the pipe in place.

Port 38 on adapter 20 and about which pipe 30 is rotated, is offset relative to the axis of rotation of adapter 20. This is clearly seen in FIG. 2, in which the axis of rotating adapter 20 is substantially horizontal as the device is viewed, whereas the rotation of pipe 30 at port 38 is about an axis forming an acute angle with the axis of rotation of the adapter. Specifically, the axis about which the pipe is rotated is preferably 45°, so that, of course, the resulting acute angle is 45°.

Pipe 30 is also preferably angled between its opposite ends 14 and 37, so that the elongated axis extending through each port at the opposite ends of the device are at different angles relative to one another. Preferably, the pipe is simply curved or bent, as shown, between its ends, to achieve that feature. Specifically, where the axis of rotation of the pipe at port 38 is 45° relative to the axis of adapter rotation, the pipe will preferably be bent or curved on an obtuse angle of 135°. If the acute angle between the axis of adapter rotation and pipe rotation is any other angle than 45°, the extent that pipe 30 is preferably bent will be at an obtuse angle between its ends which is supplementary with the acute angle beween its axis of rotation and the axis of adapter rotation. Thus, for example, if port 38 and the axis of rotation of pipe 30 therearound form a 30° angle with the axis of adapter rotation, pipe 30 will preferably be bent between its ends at an angle of 150°. Although the pipe could be bent at other angles than one which is supplementary to the acute angle difference between the axes of pipe and adapter rotation, the supplementary angle feature provides for direction the exterior pipe end 14 in any direction forward of the mask body including any direction parallel with the axis of adapter rotation. Thus, this two-way rotation of the respective adapter and pipe components allows for improved flexibility in directing the pipe as desired and for securing an oxygen supply tube from any direction, straight on or along the same axis as pipe end 14 extends.

As previously indicated, port 38 is circular, as is groove 48, adjacent pipe end 37. It will be understood that in order for pipe 30 to be rotated around port 38, both the groove and the port will need to be circular. Although a circular port 38 may be formed in any way, it is most convenient to form such a port by cutting a segment from a spherical surface along a flat plane. Thus, adapter 20 is preferably formed with a spherical exterior surface and with the circular port 38 being formed readily on that surface. Of course, if the exterior shape of adapter 20 is other than spherical, a circular surface may still be formed or molded thereon, although it may not be exactly flush with the exterior adapter surface. The preferred embodiment of having the pipe directly secured into port 38, and rotatable thereabout may be modified to achieve an equivalent function by splitting the pipe into two segments, with the exterior segment being rotatable relative to the segment secured to the adapter. In other words, an upper pipe segment may be secured in port 38, and a lower pipe segment may be rotatable relative to the upper pipe segment. However, such a construction will be more expensive than the preferred embodiment, without substantially achieving any additional improvement thereover. In another embodiment, the pipe may be attached to a fitting member, which is rotatably secured to the adapter. Thus, the pipe end itself is not required to be secured directly on the adapter. Moreover, the axes of pipe and adapter rotation as described above, need not intersect, although they do in the preferred embodiments shown.

Figures 3, 4:
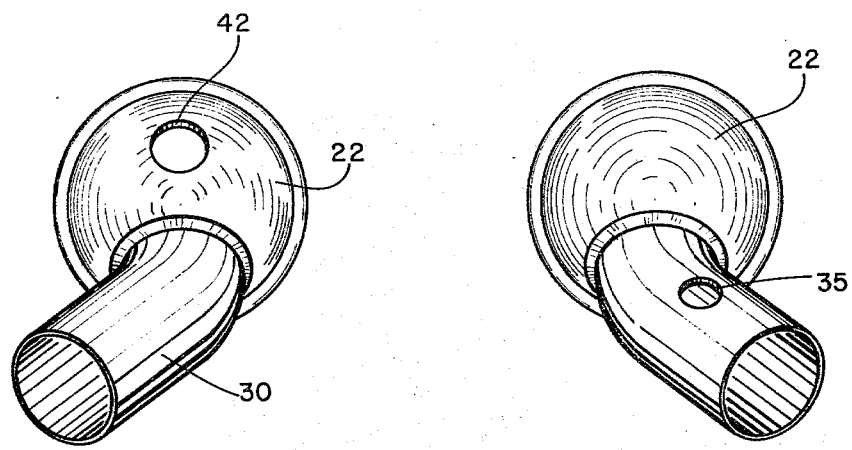
FIG. 3 is a front view of one embodiment of an adapter and pipe.
FIG. 4 is a front view of another embodiment of an adapter and pipe.
Figure 5:
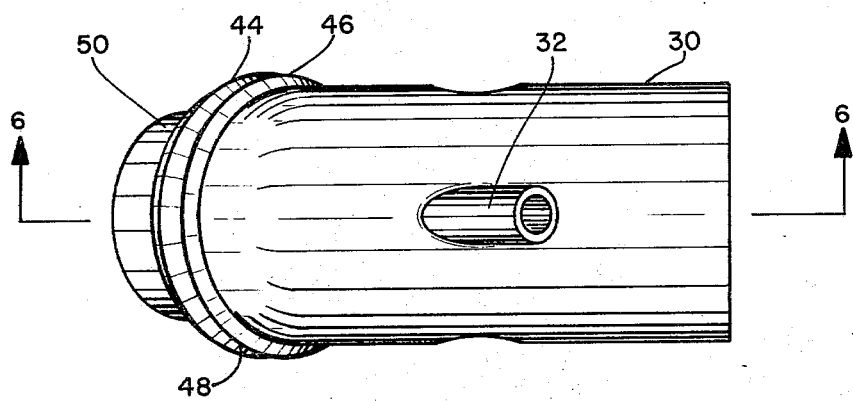
FIG. 5 is an enlarged top plan view of a pipe showing the means for attaching it to an adapter and including a calibrating member.
Figure 6:
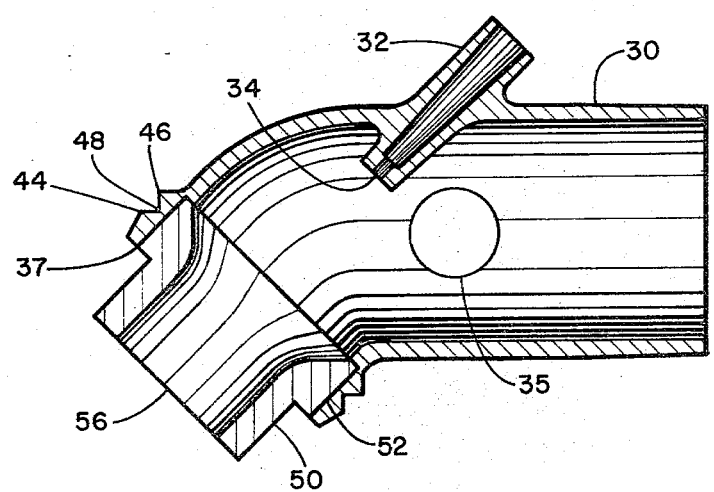
FIG. 6 is a sectional view of the pipe taken along lines 6—6 of FIG. 5.

Additional features may be incorporated into the mask of the invention as illustrated in the drawings. In FIGS. 2, 4 and 5, pipe 30 includes an exhalation port 35 through which gas expired by the patient is vented. In the device shown in FIG. 3, the exhalation port 42 is instead located on the adapter 22 rather than on pipe 30. Pipe 30 shown in FIGS. 2, 4, and 5 also has a tube 32 which extends exteriorly of the pipe and which may be connected to a gas supply source for continually directing a relatively small gas flow thereto to create a positive end expiratory pressure to the patient. Tube 32 includes a port 34 interiorly of pipe 30, so that a gas supply source directed into the tube will flow through port 37 (FIG. 2). Positive end expiratory pressure (PEEP) is well understood by those skilled in the art and need not be explained further herein. However, it is preferable that port 34 be directed along the center axis of port 37 of the pipe so that the small gas flow can be directed into the tracheotomy mask and without being baffled against a side of the device. In FIGS. 5 and 6 there is also shown a calibrating member 50, secured in port 37 of pipe 30. Since the purpose of the member is to provide a smaller port opening, different members may have different outlet port 56 sizes, or areas, or the ratio of areas of ports 34 and 56 may be varied, whereby the rate of gas flow therethrough may be correspondingly changed, and the pressure relative to the flow rate of gas through PEEP inlet tube 32 selected. In the end of pipe 30 is formed a calibrating member seat 52 adjacent port 37, and the member may be easily inserted and removed from the seat for selected use. Although the device has been described particularly as a tracheotomy mask, the invention may be used on any gas delivery mask, such as an oxygen mask, secured on a patient's face, particularly over the nose and mouth, as are well known in the art. These as well as other equivalent modifications within the purview of the invention may be incorporated as will be evident to those skilled in the art.

I claim:
1. An oxygen mask comprising
a mask body for being secured against a patient's face or throat and in sealing engagement therewith, and having an enlarged circular port,
rotatable adapter extending forwardly of said mask body having a spherical surface portion and secured on said body at said enlarged port and rotatable about a single, first axis extending normal to a plane extending across said enlarged port, and having a pipe attachment port through said spherical surface portion, the center of which pipe attachment center of which port is offset relative to said first axis, and
a pipe angled between first and second ends thereof, a first end being rotatably secured on said adapter in said pipe attachment port on said spherical surface portion and rotatable about a single second axis whereby each of said ends is directed along a different axis, said first and second axes having an acute angle therebetween whereby said port on said spherical surface and said angle between said first and second ends of said pipe are such that said adapter and said pipe are cooperatively rotatable so that said second end of said pipe may be pointed in substantially any direction forwardly of said mask body.

2. The mask of claim 1 wherein said pipe has a circular groove therearound adjacent said first end and wherein a circular edge defining said pipe attachment port is received in said circular groove.

3. The mask of claim 1 wherein said pipe includes a hollow tube projecting outwardly through a sidewall of the pipe, and having an orifice communicating interiorly of the pipe.

4. The mask of claim 3 wherein said tube orifice is aligned for directing gas along the axis of said pipe at said first end.

5. The mask of claim 4 including a removable restriction member at said first end of said pipe for reducing the opening of said pipe at said first end.

6. The mask of claim 3 including an exhalation port through the sidewall of said pipe.

7. The mask of claim 1 wherein the sum of the angle between said first and said second axes, and the angle between said first and said second ends of said pipe is 180°.

* * * * *